(12) United States Patent
Takatsuka et al.

(10) Patent No.: US 7,265,363 B2
(45) Date of Patent: Sep. 4, 2007

(54) MICROSCOPE EXAMINATION METHOD, OPTICAL STIMULATION APPARATUS, AND MICROSCOPE EXAMINATION APPARATUS

(75) Inventors: Hirofumi Takatsuka, Hachioji (JP); Yoshiharu Saito, Hachioji (JP); Yasushi Aono, Yokohama (JP)

(73) Assignee: Olympus Corporation, Tokyo (JP)

( * ) Notice: Subject to any disclaimer, the term of this patent is extended or adjusted under 35 U.S.C. 154(b) by 139 days.

(21) Appl. No.: 11/129,471

(22) Filed: May 16, 2005

(65) Prior Publication Data

US 2005/0258376 A1    Nov. 24, 2005

(30) Foreign Application Priority Data

May 24, 2004    (JP)    ............................. 2004-152994

(51) Int. Cl.
*G01N 21/64*    (2006.01)
*G21K 5/00*    (2006.01)

(52) U.S. Cl. ................................. 250/458.1; 250/459.1
(58) Field of Classification Search ............ 250/458.1, 250/459.1
See application file for complete search history.

(56) References Cited

U.S. PATENT DOCUMENTS

2003/0155527 A1*    8/2003    Natori .................... 250/458.1
2004/0001196 A1*    1/2004    Shibazaki et al. .......... 356/129
2004/0061073 A1*    4/2004    Kitagawa ................ 250/458.1

OTHER PUBLICATIONS

Atsushi Miyawaki, et al.: Special Review, Optical Techniques Using the New Fluorescent Protein Kaede, Saibou Kougaku (Cell Technology), vol. 22, No. 3, 2003, pp. 316-326.

* cited by examiner

*Primary Examiner*—David Porta
*Assistant Examiner*—Mindy Vu
(74) *Attorney, Agent, or Firm*—Kenyon & Kenyon LLP

(57) ABSTRACT

While carrying out microscope examination, it is possible to specify a position to be irradiated with optical stimulus light and to accurately apply an optical stimulus to the specified irradiation position. A microscope examination method includes a step of introducing into a specimen a substance in which a structural change is caused by irradiation with light of a first wavelength; a step of specifying an optical stimulation site in the specimen by irradiating the specimen with visible light of a second wavelength that does not cause a structural change in the substance, while examining the specimen in which the substance is introduced using a microscope examination apparatus; and a step of irradiating the specified optical stimulus site with the light of the first wavelength.

7 Claims, 9 Drawing Sheets

MICROSCOPE EXAMINATION METHOD, OPTICAL STIMULATION APPARATUS, AND MICROSCOPE EXAMINATION APPARATUS

BACKGROUND OF THE INVENTION

1. Field of the Invention

The present invention relates to a microscope examination method, an optical stimulation apparatus, and a microscope examination apparatus employed in optical marking. Optical marking utilizes a substance that produces fluorescence in response to an optical stimulus, such as a fluorescent protein or a caged compound, or that activates another fluorescent substance.

This application is based on Japanese Patent Application No. 2004-152994, the content of which is incorporated herein by reference.

2. Description of Related Art

A conventionally known microscope examination apparatus including this type of optical stimulation apparatus is the microscope examination apparatus disclosed, for example, in Atsushi Miyawaki, et al., "Special Review, Optical techniques using the new fluorescent protein kaede", Cell Technology, Vol. 22, No. 3, 2003, pp 316-326 (hereinafter referred to as reference 1).

This microscope examination apparatus is an inverted-type incident-light fluorescence microscope having an observation light source formed of a xenon lamp and a fluorescence filter for carrying out fluoroscopy. In addition, this microscope is also provided with a xenon lamp, an excitation filter, and a field stop for forming a spot of ultraviolet light serving as an optical stimulus. The optical stimulus is made incident on the specimen along the same optical axis by means of a dichroic mirror disposed in the light path of the observation light source.

With this microscope examination apparatus, the optical system, including the field stop, the focusing lens, the objective lens, and so forth, can be precisely adjusted, thus making it possible to precisely position the spot of ultraviolet light at the center of the field of view used for fluoroscopy. Therefore, the location in the object under examination, such as a cell, where the optical stimulus is to be applied can be aligned with the center of the field of view and irradiated with the spot of ultraviolet light. Thus, the optical stimulus can be accurately applied to the target cell, which allows optical marking to be carried out.

In such a case, the optical stimulus location in the object under examination is restricted to a single point at the center of the field of view in the microscope apparatus in reference 1. Therefore, when an optical stimulus is to be accurately applied to that location, it is essential to shift the relative positional relationship in directions orthogonal to the optical axis of the objective lens and the object under examination.

When examining cells and so forth, in order to maintain the viability of the cells, it is customary to carry out examination of the cells while they are disposed in a predetermined amount of liquid, such as a culture medium or the like. However, one drawback with this technique is that moving the object under examination while keeping the objective lens fixed causes the cells to move around in the liquid, thus changing the examination conditions. Also, when moving the objective lens while keeping the object under examination fixed, it is necessary to move the entire optical system including the objective lens. In order to move it with accuracy, the apparatus inevitably becomes larger and the cost is also increased. This is another drawback.

Another possible method is that in which a field stop is moved in directions orthogonal to the optical axis. This method does not suffer from the drawbacks mentioned above. However, the irradiation position of the spot of ultraviolet light is arbitrarily moved in the optical field, which differs from the methods described above in which the spot is fixed at the center of the field of view. Therefore, this method suffers from a problem in that it is difficult to accurately specify the irradiation position.

BRIEF SUMMARY OF THE INVENTION

In light of the circumstances described above, and an object of the present invention is to provide a microscope examination method, an optical stimulation apparatus, and a microscope examination apparatus in which a position in the field of view to be irradiated with optical stimulus light can be specified and the optical stimulus can be accurately applied to the specified irradiation position while carrying out microscope examination.

In order to achieve the object described above, the present invention provides the following solutions.

According to a first aspect, the present invention provides a microscope examination method including a step of introducing into a specimen a substance in which a structural change is caused by irradiation with light of a first wavelength; a step of specifying an optical stimulation site in the specimen by irradiating the specimen with visible light of a second wavelength that does not cause a structural change in the substance, while examining the specimen in which the substance is introduced using a microscope examination apparatus; and a step of irradiating the specified optical stimulus site with the light of the first wavelength.

With the microscope examination method according to the first aspect, the specimen in which the substance is introduced is irradiated with visible light of the second wavelength while observing it. When the specimen is irradiated with the visible light of the second wavelength, the visible light of the second wavelength is located at the center of the observed field of view by the microscope examination apparatus. Therefore, it is possible to easily specify the optical stimulus site while viewing the examination image. Since the visible light of the second wavelength is light that does not cause a structural change in the substance introduced in the specimen, it is possible to specify the optical stimulus site without carrying out optical marking. Then, after specifying the optical stimulus site, the specified optical stimulus site is irradiated with the light of the first wavelength, thus allowing optical marking to be performed by accurately applying an optical stimulus to the optical stimulus site.

In the aspect of the invention described above, the microscope examination apparatus is preferably formed of a fluorescence microscope that irradiates the specimen with excitation light of a third wavelength different from the first wavelength and the second wavelength to observe the fluorescence produced thereby. By making the wavelength of the excitation light different from the first and second wavelengths, it is possible to independently carry out specification of the optical stimulus site, optical stimulation, and fluoroscopy of the specimen.

Furthermore, in the aspect of the invention described above, the microscope examination apparatus is preferably a stereomicroscope. With a stereomicroscope, since the field of view is large and there is a high degree of freedom in positioning the optical stimulus site, it is necessary to accurately specify the optical stimulus site before applying the optical stimulus. With this configuration, it is therefore possible to accurately apply the optical stimulus to an optical stimulus site within a large field of view.

According to a second aspect, the present invention provides an optical stimulation apparatus including a first light source that emits light of a first wavelength that irradiates a substance introduced into a specimen to cause a structural change thereof; a second light source that emits visible light of a second wavelength, different from the first wavelength, the second wavelength not causing a structural change in the substance; an optical-axis combining unit that aligns the optical axis of the first light source and the optical axis of the second light source; and a focusing optical system that focuses the light from the first and second light sources.

With the optical stimulation apparatus according to the second aspect, when the second light source is switched on to radiate visible light of the second wavelength, which is irradiated so as to form a spot on the specimen via the focusing optical system, it is possible to form a marker on the specimen without causing any structural change in the substance introduced in the specimen. Also, the optical-axis combining unit aligns the optical axis of the light from the first light source and the optical axis of the visible light from the second light source. Therefore, when light is radiated from the first light source after specifying the optical stimulus position using the visible light from the second light source, the light from the first light source is made incident with high accuracy on the optical stimulus site specified with the second light source.

The aspect of the invention described above preferably also includes optical fibers that connect the optical-axis combining unit with the first and second light sources, respectively; and focus adjusting mechanisms that can adjust the tip positions of the optical fibers at the connection points between the optical-axis combining unit and the optical fibers.

Since the first light source and the second light source produce light with different wavelengths, the focal position changes due to chromatic aberration. Thus, by adjusting the positions of the tips of the optical fibers by operating the focus adjusting mechanisms, whenever the focal position of either of the light sources is adjusted, the focal position of the other light source can also be adjusted to match it.

Furthermore, in the aspect of the invention described above, the focusing optical system is preferably capable of being removably attached to the optical-axis combining unit.

By forming the focusing optical system and the optical-axis combining unit as two separate detachable units, the focusing optical system can be separated from the optical-axis combining unit, which allows the focusing optical system to be replaced with another one having a different focal length.

Furthermore, the aspect of the invention described above preferably also includes an optical fiber that guides the light beams whose optical axes are aligned by the optical-axis combining unit to the focusing optical system; a focus adjusting mechanism that can adjust the distance between an exit face of the optical fiber and each light source; and a chromatic-aberration correcting member, provided in the focusing optical system, for correcting aberration of the light of the first wavelength and the second wavelength.

The light beams whose optical axes are combined by the optical-axis combining unit are imaged onto one end of the optical fiber, are transmitted by the optical fiber, and are then emitted from the other end. Since the distance between each light source and the other end of the fiber, that is to say, the exit face, is adjusted by operating the focus adjusting mechanism, the light from the first and second light sources is emitted such that the exit face of the optical fiber effectively serves as an emission point. Chromatic aberration occurs due to the difference between the first wavelength and the second wavelength, causing a shift in the focal position of the focusing optical system, which is corrected by the chromatic-aberration correcting member. Correcting this aberration allows the light from the first light source and the light from the second light source to be accurately aligned and imaged at the same position.

According to a third aspect, the present invention provides an optical stimulation apparatus including a first light source that emits light of a first wavelength that irradiates a substance introduced into a specimen to cause a change in the structure thereof; a second light source that emits light of a second wavelength different from the first wavelength, the second wavelength not causing a change in the structure of the substance; and a focusing optical system that focuses the light from the first and second light sources. The first and second light sources are formed of a light source unit and filters that selectively transmit light of the first wavelength or light of the second wavelength among light from the light source unit.

With the optical stimulation apparatus according to the third aspect, light emitted from the same light source unit can be made to pass through the filters, thereby radiating light of the first wavelength and light of the second wavelength. Therefore, it is possible to specify the optical stimulus position and to carry out optical stimulation using a common light source.

According to a fourth aspect, the present invention provides a microscope examination apparatus having the optical stimulation apparatus described above, wherein the microscope examination apparatus includes an objective optical system disposed adjacent to the specimen; an illumination optical system that introduces illumination light to the objective optical system; and an eyepiece optical system that allows observation of return light from the specimen. In addition, the objective optical system includes a light introducing member that introduces light from the first and second light sources whose optical axes are aligned; an aperture that restricts the image of the first and second light sources formed on the specimen; and an aperture moving mechanism that moves the aperture in directions orthogonal to the optical axis.

With the microscope examination apparatus according to the fourth aspect, when the illumination light emitted by the illumination optical system enters the objective optical system, it is imaged onto the specimen by the objective optical system. Returning light then returns via the objective optical system and can be observed with the eyepiece optical system. On the other hand, in the objective optical system, the light beams from the first and second light sources whose optical axes are aligned are introduced by means of the light introducing member and form an image of the first and second light sources on the specimen. This image of the light sources is limited by the aperture to form a light spot. Also, moving the aperture in directions orthogonal to the optical axis by operating the aperture moving mechanism allows the light spot to be moved to any position on the specimen.

In such a case, since the light from the second light source is visible light that does not cause a structural change in the substance, return light from the specimen and reflected light of the spot formed by the visible light can be observed with the eyepiece optical system. Therefore, it is possible to move the light spot to a desired stimulus position by means of the aperture moving mechanism, while visually confirming the position of the light spot. Then, once the light spot position has been set, the light of the first wavelength from the first light source, which causes a structural change in the substance, is introduced, thereby accurately radiating optical stimulus light onto the optical stimulus position indicated by the light spot, which allows detailed examination to be carried out.

Accordingly, the present invention provides an optical stimulation apparatus that can specify an optical stimulus position and accurately radiate the specified optical stimulus position with optical stimulus light without causing a structural change in the substance introduced into the specimen.

DETAILED DESCRIPTION OF THE INVENTION

An optical stimulation apparatus according to an embodiment of the present invention will be described below with reference to FIGS. 1 and 2.

Figure 1:
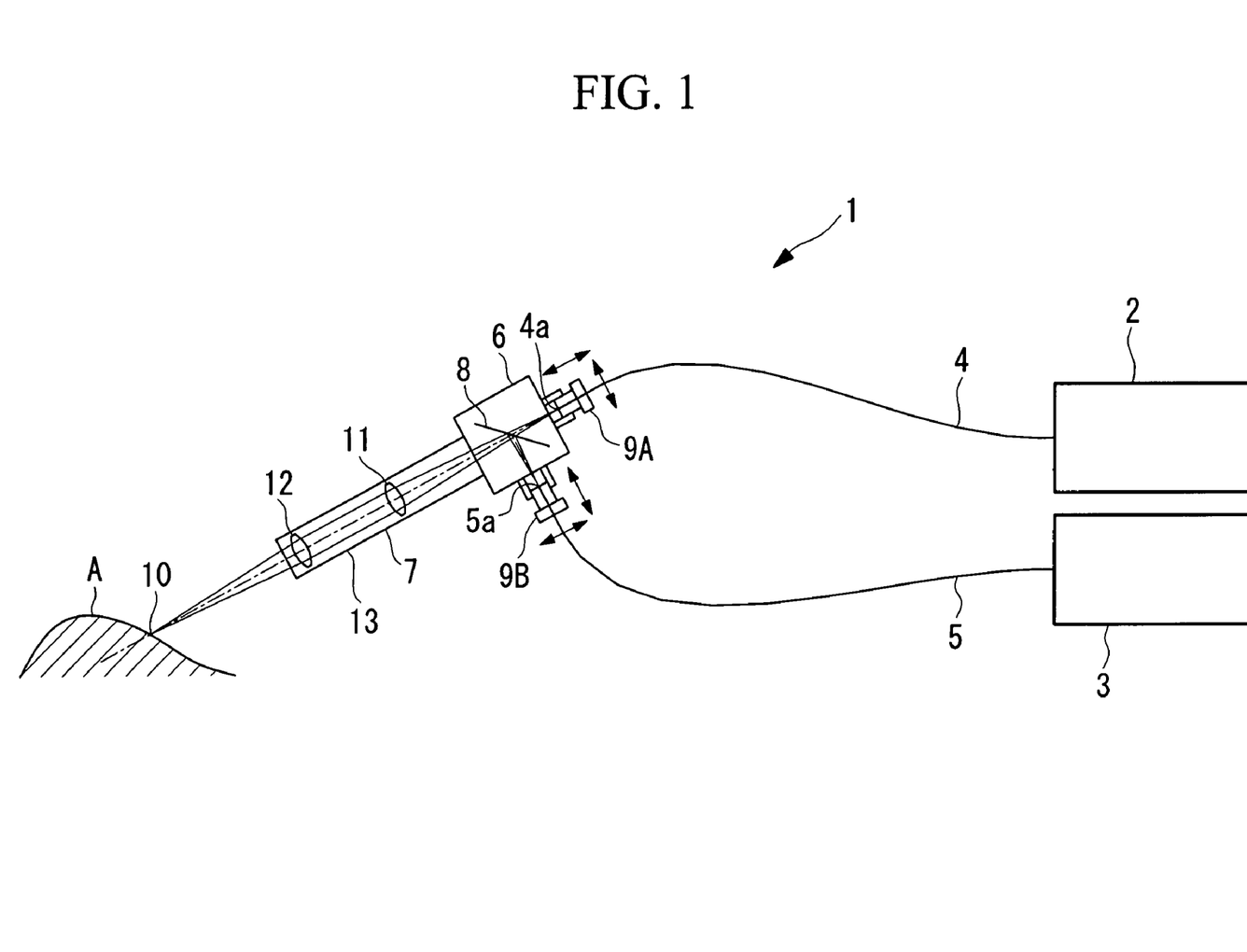
FIG. 1 is a schematic diagram showing an optical stimulation apparatus according to an embodiment of the present invention.

As shown in FIG. 1, an optical stimulation apparatus according to this embodiment includes a first light source 2 that emits light of a first wavelength; a second light source 3 that emits light of a second wavelength; optical fibers 4 and 5 that transmit light from these light sources 2 and 3, respectively; an optical-axis combining unit 6 that joins the optical fibers 4 and 5 and combines the optical axes of the optical fibers 4 and 5; and a focusing optical system 7 that focuses the light beams emitted from the optical fibers 4 and 5 along the optical axis combined by the optical-axis combining unit 6 to image them at a light spot.

The first light source 2 emits light of a wavelength that causes a structural change in a substance introduced into a specimen A, namely, a substance that produces fluorescence in response to an optical stimulus, such as a fluorescent protein or a caged compound, or that causes another fluorescent substance to be activated. On the other hand, the second light source 3 emits light of a wavelength that does not cause a structural change in these substances.

The optical-axis combining unit 6 is provided with a dichroic mirror 8 that transmits light from the first light source 2 and that reflects light from the second light source 3, thus aligning the optical axis of the light from the first light source 2 and the optical axis of the light from the second light source 3. Position adjusting mechanisms 9A and 9B that enable positional adjustment of exit faces 4a and 5a of the optical fibers 4 and 5, respectively, are also provided in the optical-axis combining unit 6.

Figure 2:
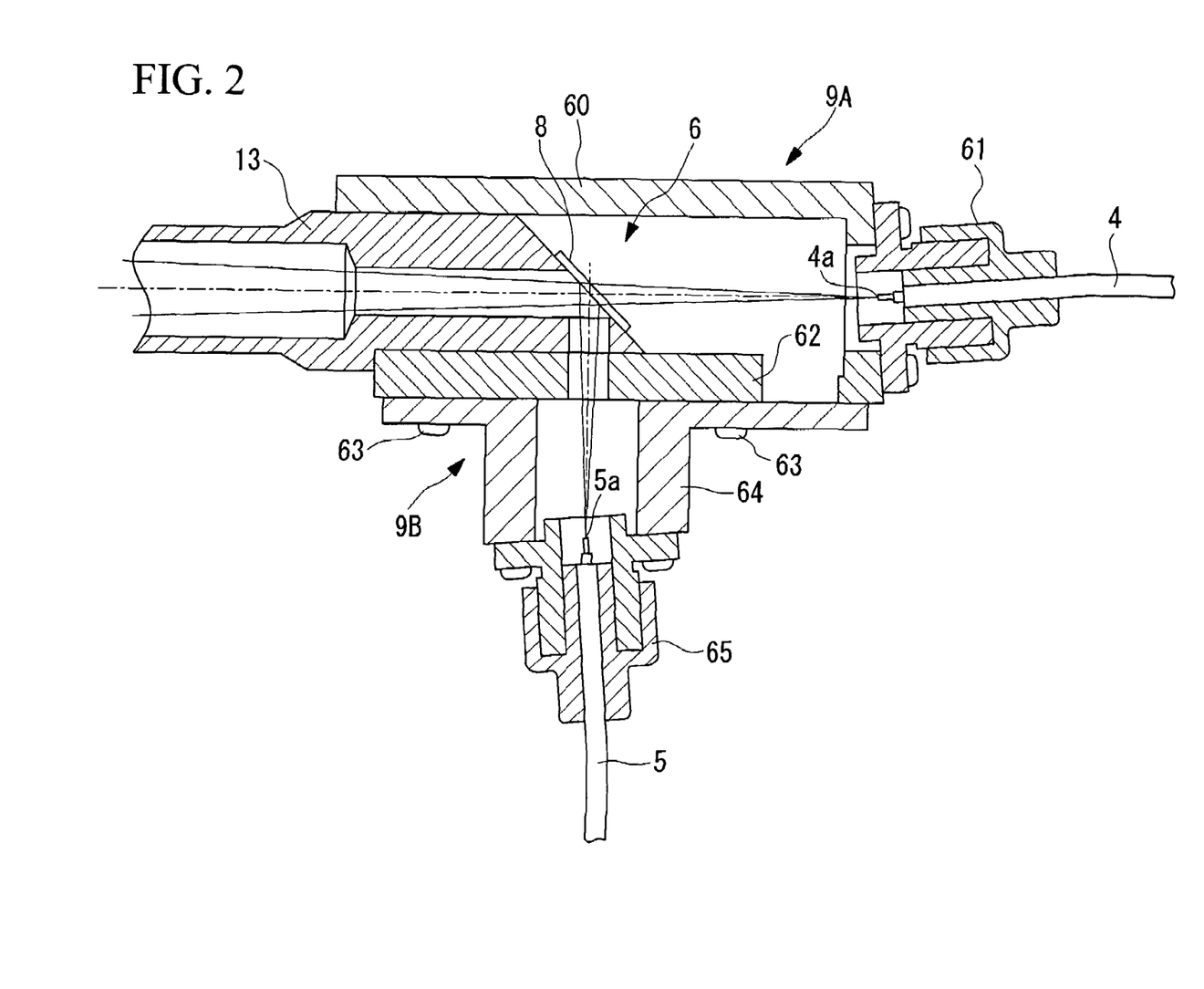
FIG. 2 is a partial longitudinal sectional view showing a position adjusting mechanism of the optical stimulation apparatus in FIG. 1.

More concretely, as shown in FIG. 2, the position adjusting mechanism 9A is constructed by attaching a sliding tube 60, which can slide in the longitudinal direction, to the outer surface of a cylindrical apparatus main body 13 constituting the focusing optical system 7 and by fixing a connector 61, which connects the optical fiber 4, to the sliding tube 60. The position adjusting mechanism 9B is constructed by attaching, by means of a screw 63, a bracket 64 to an intermediate base 62 that is fixed to the apparatus main body 13 and by fixing a connector 65, which connects the optical fiber 5, to the bracket 64.

Position adjustment of the exit face 4a of the optical fiber 4 in the optical axis direction by the first position adjusting mechanism 9A is carried out by sliding the sliding tube 60 with respect to the apparatus main body 13. Also, position adjustment of the exit face 5a of the optical fiber 5 in the optical axis direction by the second position adjusting mechanism 9B is carried out by loosening the screw 63 and inserting shims (not shown in the drawing) of specified thickness into the gap between the intermediate base 62 and the bracket 64. The inclination of the optical axis of the optical fiber 5 can be adjusted by making the thicknesses of the shims disposed on either side of the optical axis different. Furthermore, when the screw 63 is loosened, it is possible to adjust the position of the bracket 64 in a direction orthogonal to the optical axis relative to the intermediate base 62 within a range allowed by the gap between the screw 63 and a through-hole (not shown) for the screw 63, which is provided in the bracket 64.

Figure 3:
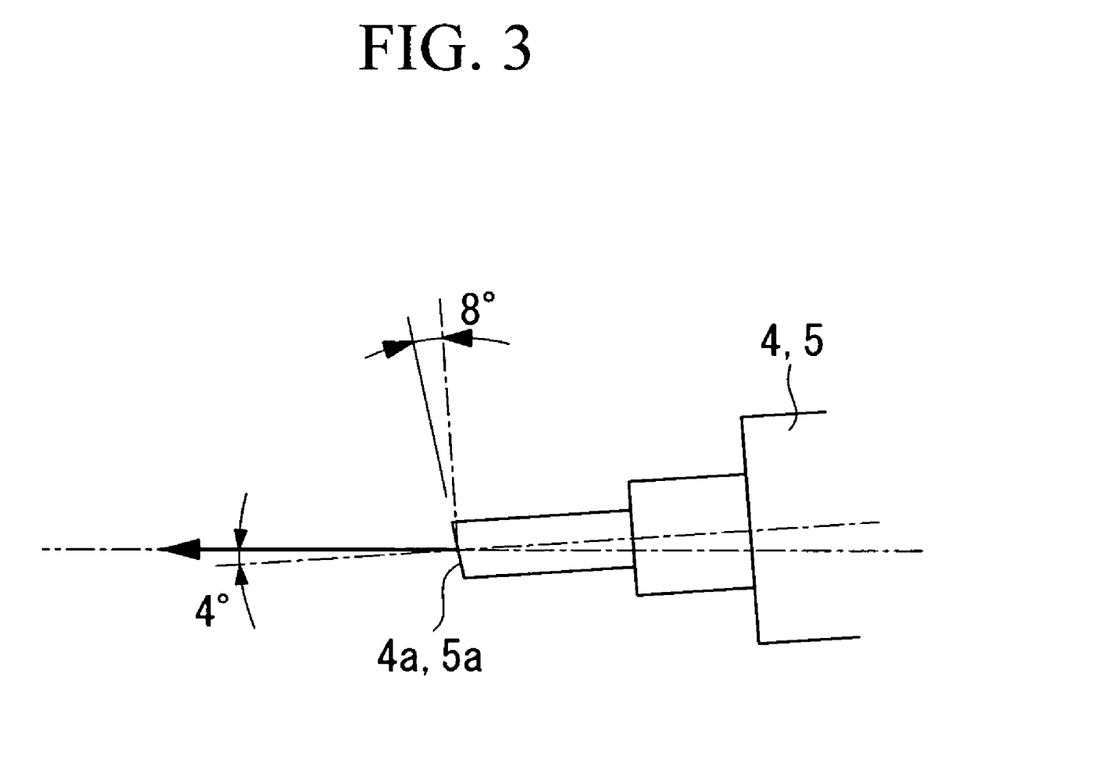
FIG. 3 shows the inclination of exit faces of optical fibers in the optical stimulation apparatus in FIG. 1.

The connectors 61 and 65 are attached at an angle with respect to the sliding tube 60 or the bracket 64. As shown in FIG. 3, this inclination angle is approximately 4°, and the exit faces 4a and 5a of the optical fibers 4 and 5 are cut at an angle of approximately 8°. With this configuration, part of the light transmitted in the optical fibers 4 and 5 can be prevented from returning back along the optical fibers 4 and 5 due to reflection at the exit faces 4a and 5a.

Since exit faces 4a and 5a of the optical fibers 4 and 5 and the focal point of the focusing optical system 7 are disposed at mutually conjugate positions, the exit faces 4a and 5a of the optical fibers 4 and 5 can be moved in their optical-axis directions by operating the position adjusting mechanisms 9A and 9B, which allows a focal position 10 disposed in front of the focusing optical system 7 to be adjusted in the optical axis direction for each of the optical fibers 4 and 5. Also, by operating the position adjusting mechanism 9B, the exit face 5a of the optical fiber 5 can be moved in directions orthogonal to the optical axis, which enables the position of the focal point 10 of the light from the light source 3 to be adjusted in directions orthogonal to the optical axis. Likewise, the position adjusting mechanism 9A may also be provided with a structure that enables position adjustment in directions orthogonal to the optical axis.

The focusing optical system 7 includes a collimator lens 11 that converts the light beams from the exit faces 4a and 5a of the optical fibers 4 and 5 on the optical axis combined in the optical-axis combining unit 6 into collimated beams; and an objective lens 12 that forms an image at a predetermined position. The collimator lens 11 and the objective lens 12 are contained inside the cylindrical apparatus body 13.

Figure 4:
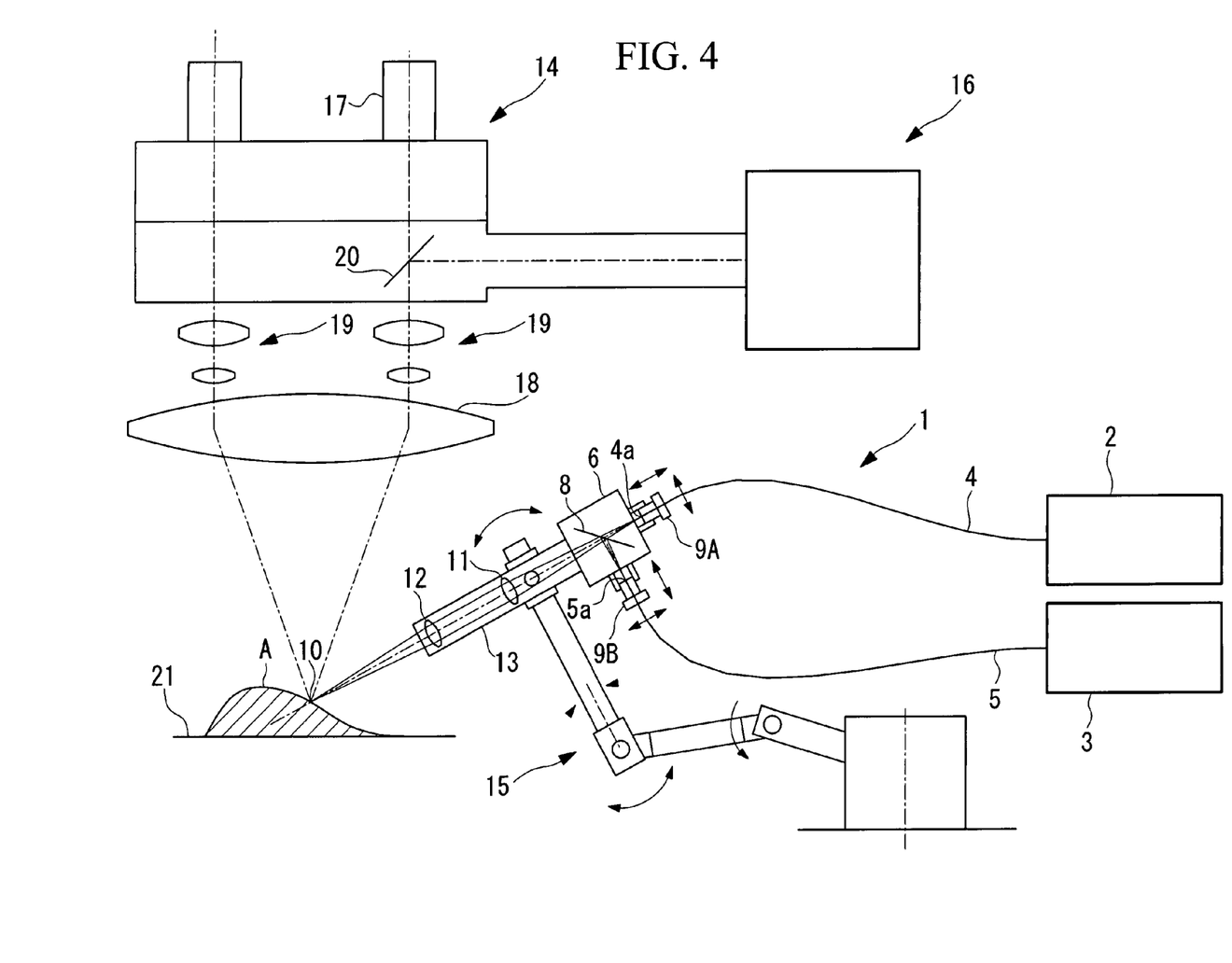
FIG. 4 is a schematic diagram showing a microscope examination apparatus employing the optical stimulation apparatus of FIG. 1.

By fixing the optical stimulation apparatus 1 according to this embodiment to a manipulator 15 disposed adjacent to a microscope examination apparatus, such as a stereomicroscope 14, as shown in FIG. 4 for example, and operating the manipulator 15, the position and orientation thereof can be set as desired. The stereomicroscope 14 shown in FIG. 2 is a Galilean stereomicroscope 14 including an illumination device 16, a binocular eyepiece optical system 17, a large objective lens 18, and a zoom mechanism 19. A dichroic mirror 20 that reflects excitation light from the illumination device 16 and that transmits fluorescence from the specimen A is provided in the light path running from the eyepiece optical system 17 to the zoom mechanism 19. The specimen A is mounted on a stage 21.

The operation of the optical stimulation apparatus 1 according to this embodiment, having such a configuration, will be described below.

When performing optical stimulation of the specimen A with the optical stimulation apparatus 1 of this embodiment, first, a substance whose structure changes in response to light of the first wavelength is introduced into the specimen A. This material is a substance that produces fluorescence in response to an optical stimulus, such as, for example, a fluorescent protein or caged compound, or alternatively, a substance that activates another fluorescent material.

Next, before irradiating the specimen A with light, the position adjusting mechanisms 9A and 9B are adjusted to align the image position at which an image of the first light source 2 is formed via the optical fiber 4 from the first light source 2, the optical-axis combining unit 6, and the focusing optical system 7 and the image position at which an image of the second light source 3 is formed via the optical fiber 5 from the second light source 3, the optical-axis combining unit 6, and the focusing optical system 7.

The first light source 2 is then switched off and only the second light source 3 is operated to emit light of the second wavelength. In this state, the manipulator 15 is operated to position the image of the second light source 3 in the field of view of the stereomicroscope 14. Since the light from the second light source 3 is visible light, the operator can easily position it within the field of view of the stereomicroscope 14. By doing so, the condition of the specimen A and the light spot formed on the specimen A can both be observed using the stereomicroscope 14. Thus, the operator manipulates the manipulator 15 so that the image of the second light source 3 is formed within the field of view of the stereomicroscope 14 and positions the light spot formed of the image of the second light source 3 at a desired stimulus position within the field of view.

Since the light from the second light source 3 is visible light, the operator can easily position the light spot at the desired stimulus position. Also, the light from the second light source 3 has a wavelength that does not cause a structural change of the substance introduced into the specimen A. Therefore, even though it is imaged onto the specimen A, it does not cause any structural change in the substance, and it is thus possible to specify the optical stimulus position without producing fluorescence and without activating another substance.

Next, the second light source 3 is switched off and light from the first light source 2 is imaged onto the specimen A. By operating the position adjusting mechanisms 9A and 9B, the image position of the light from the first light source 2 can be aligned with the previous image position of the light from the second light source 3. In addition, since the optical axes of the light from both light sources 2 and 3 are aligned by the optical-axis combining unit 6, the light from the first light source 2 is imaged at an accurately aligned point at the optical stimulus position where the spot of light from the second light source 3 was positioned. As a result, it is possible to accurately radiate light from the first light source 2 at the optical stimulus position indicated by the light from the second light source 3.

Since the light emitted from the first light source 2 has a wavelength that causes a structural change in the substance introduced into the specimen A, the structure of the substance changes in response to the light emitted from the first light source 2, and in examination carried out thereafter by a fluorescence microscope, the substance emits fluorescence in response to excitation light irradiated thereon. Alternatively, another substance may be activated to emit fluorescence.

For example, if the substance introduced into the specimen A is the fluorescent protein kaede, by adjusting the irradiation time of the light of the first wavelength emitted from the first light source 2, during subsequent observation using the fluorescence microscope, it is possible to change the color of the fluorescence produced from green to yellow and from yellow to red. If the substance introduced into the specimen A is the fluorescent protein PA-GFP, by irradiating the light of the first wavelength, green fluorescence is produced during the subsequent observation with the fluorescence microscope.

Furthermore, if the substance introduced into the specimen A is caged calcium, by irradiating it with the light of the first wavelength emitted from the first light source 2, calcium ions are released from the caged compound and are discharged, and the surrounding cells thus receive a stimulus by means of the calcium ions. As a result, during subsequent observation with the fluorescent microscope, the surrounding cells, or likewise, a calcium indicator, produce fluorescence. If the substance introduced into the specimen A is a caged NO compound, by irradiating it with light of the first wavelength emitted from the first light source 2, NO is discharged from the caged NO compound and can stimulate the surrounding cells.

In other words, it is possible to accurately conduct optical marking, using the light from the first light source 2, at any position in the specimen A specified by the visible light from the second light source 3.

Figure 5:
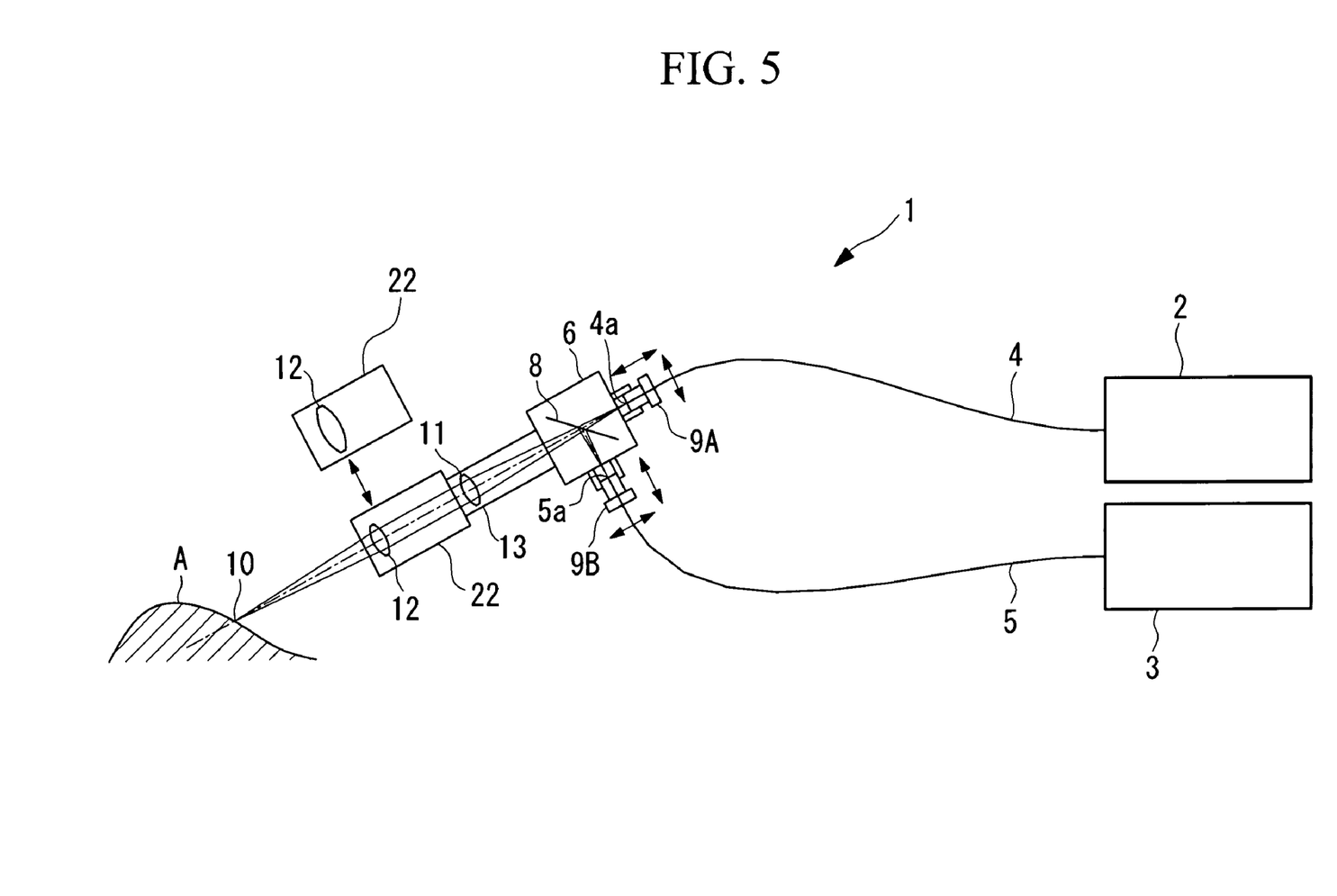
FIG. 5 is a schematic diagram showing a modification of the optical stimulation apparatus in FIG. 1.

In the embodiment described above, the collimator lens 11 and the objective lens 12 functioning as the focusing optical system 7 are contained inside the apparatus main body 13; however, instead of this, as shown in FIG. 5, the collimator lens 11 may be disposed inside the apparatus main body 13 while the objective lens 12 may be attachable to and detachable from the apparatus main body 13, as an objective lens unit 22. With this configuration, the objective lens unit 22 can be replaced with another one having a different focal length.

Figure 6:
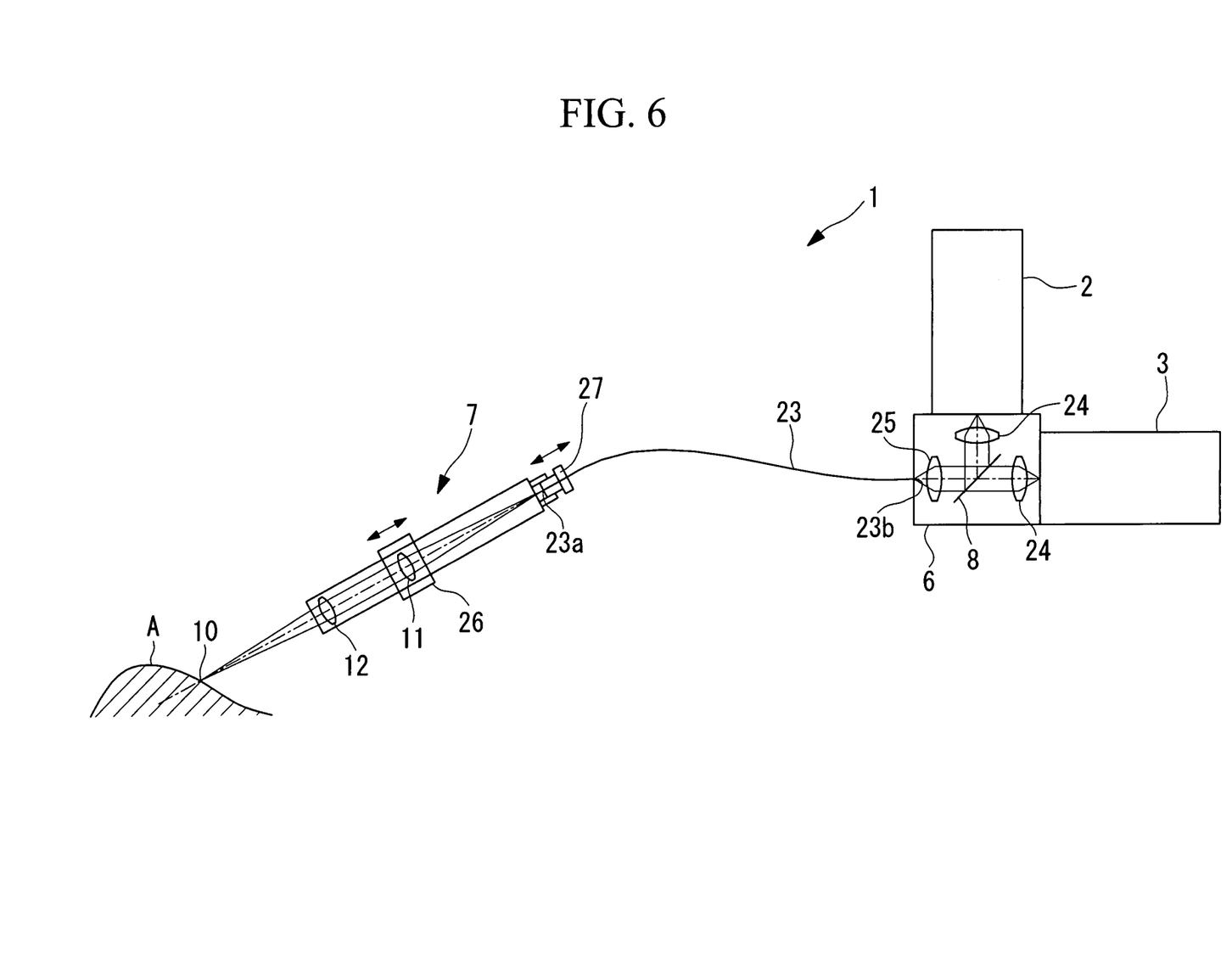
FIG. 6 is a schematic diagram showing another modification of the optical stimulation apparatus in FIG. 1.

As shown in FIG. 6, the optical-axis combining unit 6 and the focusing optical system 7 including the collimator lens 11 and the objective lens 12 may be separated from each other and coupled by an optical fiber 23. A collimator lens 24 and a focusing lens 25 are disposed inside the optical-axis combining unit 6, and light from the light sources 2 and 3 is focused onto an end 23b of the optical fiber 23. In this case, since the end of the optical fiber 23 serves as a common image plane for the first light source 2 and the second light source 3, the focal position shifts due to chromatic aberration in the same collimator lens 11 and objective lens 12. As a result, chromatic-aberration correcting members 26 and 27 for correcting the chromatic aberration are provided in the focusing optical system 7. The chromatic-aberration correcting member 26 is, for example, a moving mechanism that moves the collimator lens 11 or the exit face 23a in the optical axis direction depending on the wavelength of the radiated light.

With this configuration, an additional component, namely, the chromatic-aberration correction member 26, is required, but on the other hand, it is possible to use only a single optical fiber 23 to connect the light sources 2 and 3 with the focusing optical system 7. Therefore, the focusing optical system 7 can be easily repositioned, which affords an advantage in that it is possible to apply an optical stimulus to the specimen A from any angle and position.

Figure 7:
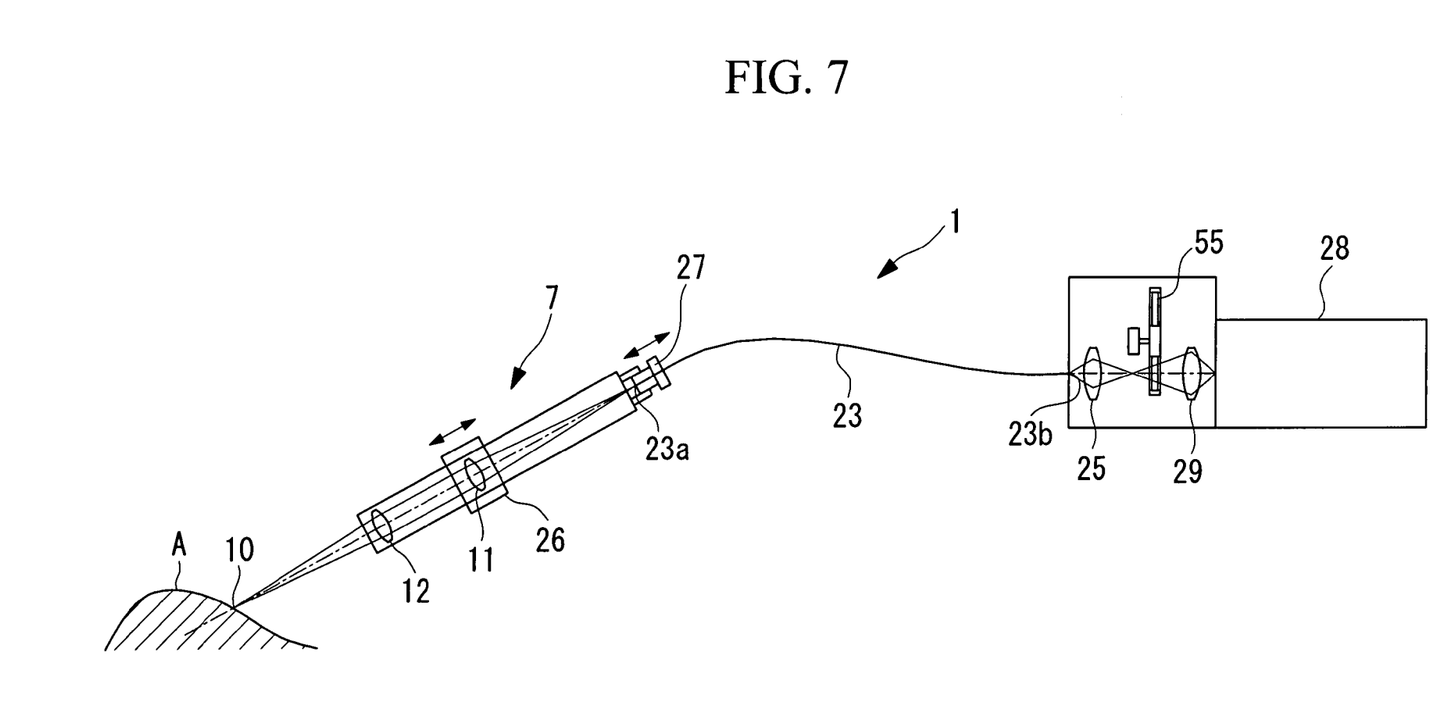
FIG. 7 is a schematic diagram showing another modification of the optical stimulation apparatus in FIG. 1.

As shown in FIG. 7, a single light source (light source unit) 28 and filters 55 that can selectively emit light of a first wavelength and light of a second wavelength may be used. Reference numeral 29 in the figure represents a focusing lens. By selecting the filters 55 to emit light of the second wavelength when specifying the optical stimulus position and to emit light of the first wavelength when applying the optical stimulus, it is possible to achieve the same results as described above. Using a single light source allows the apparatus to be made more compact.

Next, a microscope examination apparatus 30 according to an embodiment of the present invention will be described with reference to FIG. 8.

Figure 8:
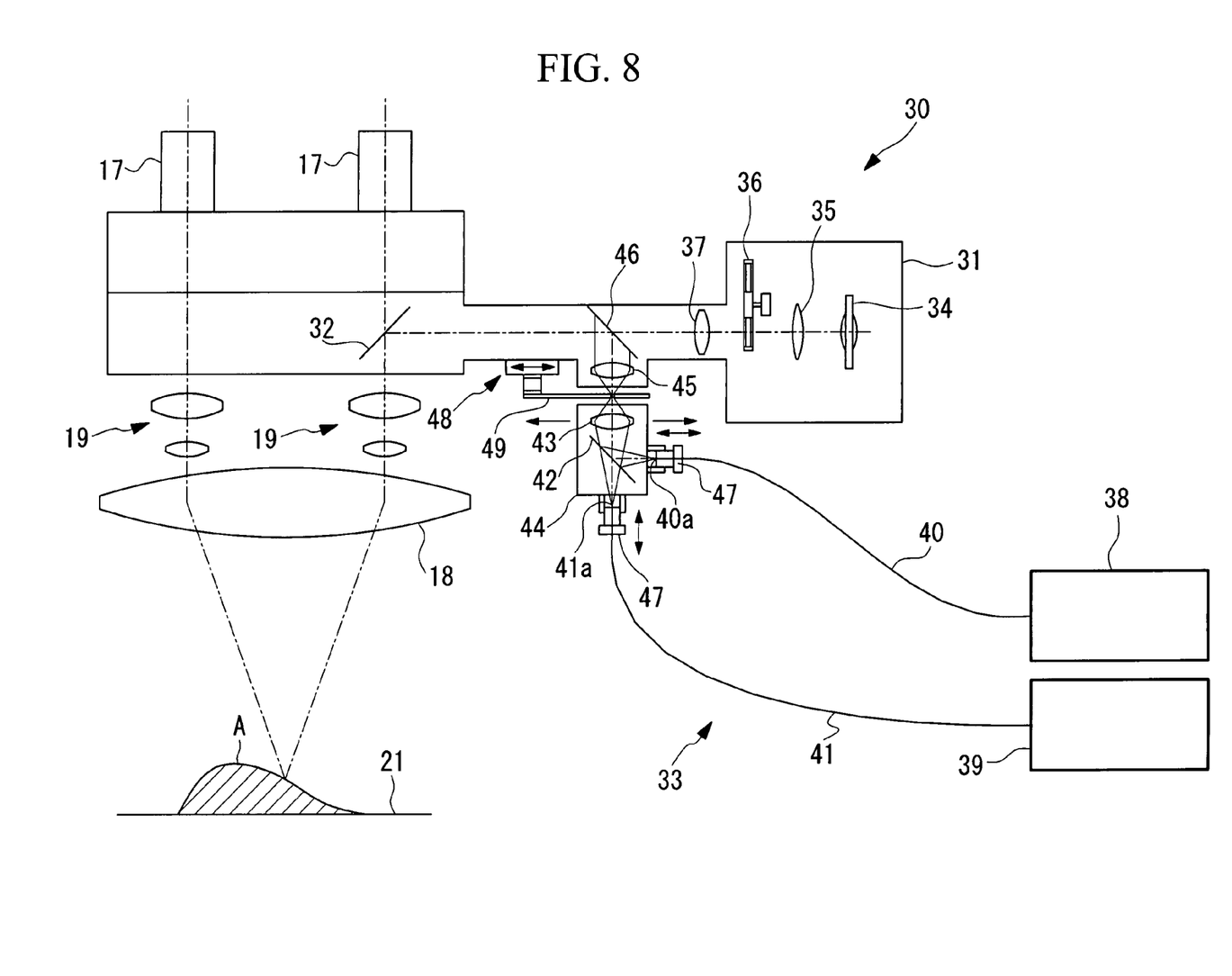
FIG. 8 is a schematic diagram showing a microscope examination apparatus according to an embodiment of the present invention.

As shown in FIG. 8, the microscope examination apparatus 30 according to this embodiment is a Galilean fluorescence stereoscopic microscope examination apparatus like that shown in FIG. 4. It has a construction in which an optical stimulation apparatus 33 is connected to the light path running from an illumination device 31 to a dichroic mirror 32.

As shown in FIG. 8, the illumination device 31 includes a xenon lamp 34, a focusing lens 35, an excitation filter turret 36, and a collimator lens 37. Light emitted from the xenon lamp 34 is transmitted through the excitation filter turret 36, and is incident on the collimator lens 37 as excitation light having a desired wavelength. The wavelength of the excitation light is different from the first wavelength and the second wavelength of the optical stimulation apparatus 33, which is described later, and does not cause any structural change in the substance. Also, a through-hole (not shown) for introducing visible light to the collimator lens 37 is included in the excitation filter turret 36 for allowing light from the xenon lamp 34 to pass directly therethrough.

The optical stimulation apparatus 33 according to this embodiment includes a first light source 38 that emits light of a first wavelength; a second light source 39 that emits light of a second wavelength; optical fibers 40 and 41 that transmit light from these light sources 38 and 39, respectively; an optical-axis combining unit 44 including a dichroic mirror 42 that joins the optical fibers 40 and 41 and that couples the optical axes from both optical fibers 40 and 41, and a focusing lens 43 that focuses light emitted from the optical fibers 40 and 41 along the axis combined by the dichroic mirror 42; a collimator lens 45 that collimates the light focused by the focusing lens 43; and a dichroic mirror 46 that makes the collimated light coincident with the optical axis of the illumination device 31.

The first light source 38 emits light of a wavelength that causes a structural change in the substance introduced into the specimen A, namely, a substance that produces fluorescence in response to an optical stimulus, such as a fluorescent protein or a caged compound, or that causes another fluorescent substance to be activated. On the other hand, the second light source 39 emits light of a wavelength that does not cause a structural change in these substances.

The optical-axis combining unit 44 includes a focus adjusting mechanism 47 that can adjust the positions of the exit faces 40a and 41a of the optical fibers 40 and 41 in the directions of the optical axes thereof and in directions orthogonal to the optical axes; and a spot-position adjusting mechanism 48 that moves the optical-axis combining unit 44 in directions orthogonal to the combined optical axis thereof. Since the spot-position adjusting mechanism 48 two-dimensionally moves an aperture member 49 disposed between the focusing lens 43 and the collimating lens 45 in directions orthogonal to the optical axis, it is linear motion mechanism having two orthogonal axes and may be constructed of any mechanism such as a ball screw or linear guide.

A microscope examination method using the microscope examination apparatus 30 according to this embodiment, having such a configuration, will be described below.

First, before mounting the specimen A on the stage 21, the focal positions formed in front of the objective lens 18 are adjusted so as to be aligned with respect to each other by operating the focus adjusting mechanisms 47 to move the exit faces 40a and 41a of the optical fibers 40 and 41 along the optical axes thereof. Also, a substance whose structure changes in response to light of the first wavelength, for example, a fluorescent protein or a caged compound, is introduced into the specimen A.

Next, to carry out examination using the microscope examination apparatus 30 according to this embodiment, the through-hole of the excitation filter turret 36 of the illumination apparatus 31 is selected to allow light from the xenon lamp 34 to be directly incident on the collimator lens 37. The light then passes through the dichroic mirror 32, the zoom mechanism 19, and the objective lens 12 and irradiates the specimen A, and then reflected light from the specimen A is observed in the eyepiece optical system 17.

In this state, while the first light source 38 is switched off, visible light of the second wavelength is emitted only from the second light source 39. Accordingly, a stereo image of the specimen A and the light spot formed by the second light source 39 are observed by the operator, who looks through the eyepiece optical system 17. The operator then operates the spot-position adjusting mechanism 48 while looking through the eyepiece optical system 17 and moves the optical-axis combining unit 44 in directions orthogonal to the combined optical axis thereof. Thus, since the light spot in the field of view of the eyepiece optical system 17 is moved on the stereo image of the specimen A, the operator can position the light spot at a point on the stereo image where the optical stimulus is to be applied, and then stops adjusting the spot-position adjusting mechanism 48 at that position.

Since the visible light of the second wavelength is light that does not cause a structural change in the substance introduced into the specimen A, the position where the optical stimulus is to be applied can be specified without causing optical marking in the substance.

Next, the second light source 39 is switched off and the first light source 38 is operated. The light of the first wavelength is radiated from the first light source 38. The light spot position formed by the first light source 38 and the light spot position formed by the second light source 39 are aligned by operating the focus adjusting mechanisms 47 and the spot-position adjusting mechanism 48. Therefore, the light of the first wavelength can be made to accurately irradiate a point indicated by the visible light of the second wavelength to apply an optical stimulus to the specimen A.

After applying the optical stimulus for a predetermined duration, depending on the type of substance introduced into the specimen A, the first light source 38 and the second light source 39 are switched off, and the fluorescence filter in the fluorescence filter turret 36 in the illumination device 31 is selected to irradiate the specimen A with excitation light from the illumination device 31. Accordingly, fluorescence can be produced from the point where the optical stimulus is applied.

In other words, with the microscope examination apparatus 30 according to this embodiment, an advantage is afforded in that it is possible to carry out examination of that optical stimulus point or the surrounding region without moving the specimen A from the state in which the optical stimulus is applied.

Figure 9:
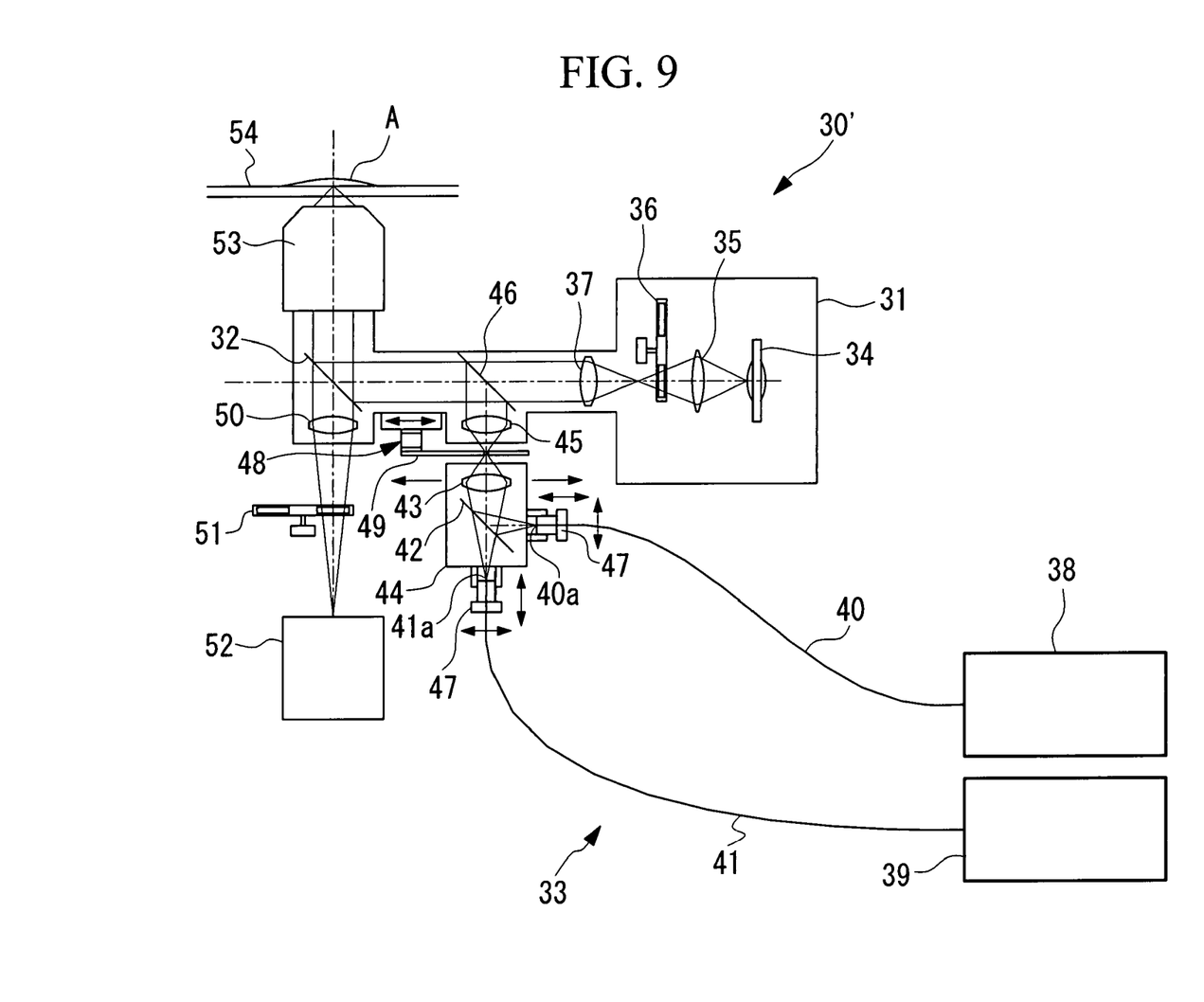
FIG. 9 is a schematic diagram showing a modification of the microscope examination apparatus in FIG. 8.

In the microscope examination apparatus 30 according to this embodiment, a stereomicroscope examination apparatus is employed and the optical stimulation apparatus 33 is connected between the illumination device 31 and the objective lens 12 thereof. Instead of this, however, as shown in FIG. 9, a configuration including the same optical stimulation device 33 in an inverted microscope examination apparatus 30' is also possible. In this figure, reference numeral 50 in the drawing represents a focusing lens, reference numeral 51 represents a fluorescence filter, reference numeral 52 represents a CCD camera, reference numeral 53 represents an objective lens, and reference numeral 54 represents a slide glass.

What is claimed is:

1. A microscope examination method comprising:
    a step of introducing into a specimen a substance in which a structural change is caused by irradiation with light of a first wavelength;
    a step of specifying an optical stimulation site in the specimen by irradiating the specimen with visible light of a second wavelength that does not cause a structural change in the substance, while examining the specimen in which the substance is introduced using a microscope examination apparatus; and
    a step of irradiating the specified optical stimulus site with the light of the first wavelength.

2. The microscope examination method according to claim 1, wherein the microscope examination apparatus is formed of a fluorescence microscope that irradiates the specimen with excitation light of a third wavelength different from the first wavelength and the second wavelength to observe the fluorescence produced thereby.

3. A microscope examination method according to claim 1, wherein the microscope examination apparatus is a stereomicroscope.

4. An optical stimulation apparatus comprising:
    a first light source that emits light of a first wavelength that irradiates a substance introduced into a specimen to cause a structural change thereof;
    a second light source that emits visible light of a second wavelength, different from the first wavelength, the second wavelength not causing a structural change in the substance;
    an optical-axis combining unit that aligns the optical axis of the first light source and the optical axis of the second light source; and
    a focusing optical system that focuses the light from the first and second light sources, wherein the focusing optical system is removably attached to the optical-axis combining unit.

5. An optical stimulation apparatus according to claim 4, further comprising:
    optical fibers that connect the optical-axis combining unit with the first and second light sources, respectively; and
    focus adjusting mechanisms that can adjust the tip positions of the optical fibers at the connection points between the optical-axis combining unit and the optical fibers.

6. An optical stimulation apparatus according to claim 4, further comprising:
    an optical fiber that guides the light beams whose optical axes are aligned by the optical-axis combining unit to the focusing optical system;
    a focus adjusting mechanism that can adjust the distance between an exit face of the optical fiber and each light source; and
    a chromatic-aberration correcting member, provided in the focusing optical system, for correcting aberration of the light of the first wavelength and the second wavelength.

7. A microscope examination apparatus including the optical stimulation apparatus according to claim 4, the microscope examination apparatus comprising:
    an objective optical system disposed adjacent to the specimen;
    an illumination optical system that introduces illumination light to the objective optical system; and
    an eyepiece optical system that allows observation of return light from the specimen;
    wherein the objective optical system is provided with:
        a light introducing member that introduces light from the first and second light sources whose optical axes are aligned;
        an aperture that limits the image of the first and second light sources formed on the specimen; and
        an aperture moving mechanism that moves the aperture in directions orthogonal to the optical axis.

* * * * *